United States Patent [19]

Roth, Jr. et al.

[11] 4,187,152

[45] Feb. 5, 1980

[54] EXTRACTIVE DISTILLATION FOR SEPARATING KETONES AND/OR ALCOHOLS FROM PHENOL AND/OR CRESOL

[75] Inventors: David W. H. Roth, Jr., Convent Station; David Zudkevitch, Denville, both of N.J.

[73] Assignee: Allied Chemical Corporation, Morris Township, Morris County, N.J.

[21] Appl. No.: 974,457

[22] Filed: Dec. 29, 1978

[51] Int. Cl.² .................. B01D 3/40; C07C 37/22; C07C 45/24; C07C 29/30
[52] U.S. Cl. .......................... 203/62; 203/63; 260/586 R; 568/749; 568/835
[58] Field of Search ............... 203/62, 63; 260/586 R, 260/586 P; 568/749, 835, 913

[56] References Cited

U.S. PATENT DOCUMENTS

| | | | |
|---|---|---|---|
| 2,265,939 | 12/1941 | Field | 203/64 |
| 2,762,760 | 9/1956 | Walker | 203/96 |
| 4,016,049 | 4/1977 | Fozzard et al. | 203/60 |
| 4,019,965 | 4/1977 | Fozzard | 203/60 |
| 4,021,490 | 5/1977 | Hudson | 203/58 |
| 4,115,204 | 9/1978 | Murtha et al. | 203/60 |
| 4,115,205 | 9/1978 | Murtha | 203/60 |
| 4,115,206 | 9/1978 | Murtha | 203/60 |
| 4,115,207 | 9/1978 | Murtha | 203/60 |

*Primary Examiner*—Wilbur L. Bascomb, Jr.
*Attorney, Agent, or Firm*—Horst M. Kasper; Gerhard H. Fuchs

[57] ABSTRACT

An extractive distillation process for separating one or more members of the group consisting of alkanols, alkanones, cycloalkanols and/or cycloalkanones from mixtures with phenol and/or cresol. One or more members of the group consisting of alkylated or unmodified cycloalkyl or aryl-derivatives of cyclohexanone or cyclohexanol having up to about 22 carbon atoms are employed as extractive solvent.

12 Claims, No Drawings

EXTRACTIVE DISTILLATION FOR SEPARATING KETONES AND/OR ALCOHOLS FROM PHENOL AND/OR CRESOL

FIELD OF THE INVENTION

This invention relates to the separation of alkanols, alkanones, cycloalkanols and/or cycloalkanones from mixtures with phenol and/or cresol.

BACKGROUND OF THE INVENTION

Cyclohexanol and cyclohexanone can be prepared by catalytic hydrogenation of phenol and by other methods such as cleavage of cyclohexylbenzene. In general, hydrogenation of phenol is incomplete and it is necessary to separate unreacted phenol from the products. Further in the oxidation of cyclohexylbenzene, phenol and cyclohexanone are formed as reaction products and must be separated. Cyclohexanol and cyclohexanone both form azeotropes with phenol making their complete recovery by fractional distillation impossible.

E. Field in U.S. Pat. No. 2,265,939, issued Dec. 9, 1941, discloses that compounds containing two alcoholic hydroxy groups such as glycol can be employed for separating phenol from cyclohexanol and/or cyclohexanone.

H. M. Walker in U.S. Pat. No. 2,762,760, issued Sept. 11, 1956, discloses extractive distillation of phenol-containing mixtures of cyclohexanone or cyclohexanol with water.

G. B. Frozzard et al. in U.S. Pat. No. 4,016,049, issued Apr. 5, 1977, disclose separation of phenol/cyclohexanone azeotrope by extractive distillation with an adipic acid diester.

Murtha et al. in U.S. Pat. Nos. 4,115,204; 4,115,205; 4,115,206; and 4,115,207 issued Sept. 19, 1978, disclose phenol-, cyclohexanone-, and cyclohexylbenzene-containing mixtures are extractively distilled to provide overhead of cyclohexanone and a kettle product substantially free of cyclohexanone by employing an N,N-disubstituted amide; an N-substituted lactam, an organic carbonate or a trisubstituted phosphate extractive agent.

SUMMARY OF THE INVENTION

In accordance with the present invention, one or more members of the group consisting of alkanols, alkanones, cycloalkanols and/or cycloalkanones are separated from mixtures with phenol and/or cresol. By subjecting such mixtures to extractive distillation conditions in the presence of an extractive solvent comprising one or more members of the group consisting of alkylated or unmodified cycloalkyl or aryl derivatives of cyclohexanone or cyclohexanol having up to about 22 carbon atoms.

DETAILED DESCRIPTION OF THE INVENTION

The present invention provides a method of separating of one or more members of the group consisting of alkanols, alkanones, cycloalkanols and/or cycloalkanones from mixtures with phenol and/or cresol where separation cannot be achieved by simple fractional distillation because of formation of azeotrope or vapor liquid equilibrium pinch.

The separation is readily achieved by extractive distillation in the presence of one or more members of the group consisting of alkylated or unmodified cycloalkyl or aryl derivatives of cyclohexanone or cyclohexanol having up to about 22 carbon atoms. The term cresol is intended to include o-cresol, m-cresol, p-cresol and mixtures thereof.

The alkanols, alkanones, cycloalkanols and/or cycloalkanones of the invention are ketones and/or alcohols having from about five to nine carbon atoms based on saturated acyclic or cyclic aliphatic hydrocarbons. The acyclic hydrocarbon part can be either straight or branched. The alkanols include n-hexanol-1, n-heptanol-1, 2-methyl pentanol-1, and cyclohexyl methanol. The alkanones include n-hexanone-1, n-heptanone-1, methyl butyl ketone, and dipropylketone. The cycloalkanols include cyclohexanol, 2-methyl-cyclohexanol, and 4-ethylcyclohexanol. The cycloalkanones include cyclohexanone, 2-methyl-cyclohexanone, and 4-ethyl-cyclohexanone.

Preferred members of the group consisting of alkanols, alkanones, cycloalkanols and cycloalkanones are cyclohexanone, cyclohexanol and their monomethyl derivatives. Cyclohexanone and cyclohexanol are the most preferred members of the group.

The extractive solvent contains one or more members of the group consisting of cycloalkanols and/or cycloalkanones derived from cyclohexanone and/or cyclohexanol and having up to about 22 carbon atoms.

The extractive solvents of the present invention include alkyl-, cycloalkyl-, dicycloalkyl- and phenyl-cycloalkyl ketones and alkyl-, cycloalkyl-, dicycloalkyl- or phenylcycloalkylalcohols with up to about 22 carbon atoms.

Preferred extractive solvents include hydrocarbylbicyclic derivatives of cyclohexanone or cyclohexanol with phenyl, benzyl and/or cyclohexyl substituents, optionally further substituted with one or more alkyl-, cyclohexyl-, benzyl and/or phenyl groups adding less than nine carbon atoms to the bicyclic system.

The number of carbon atoms in the extractive solvent is preferably from about 12 to 15. Preferred extractive solvents include cyclohexyl- and phenyl-cyclohexanone and cyclohexyl and phenyl cyclohexanol. The boiling point of the constituents of the extractive solvent are generally below about 300° C. and preferably below about 200° C.

Representative cyclohexanone derivatives useful as extractive solvents include 2-bicyclo[2.2.1]hept-2-yl-4-methyl-cyclohexanone, 2-bicyclo[2.2.1]hept-2-yl-5-methyl-cyclohexanone, 2-bicyclo[2.2.1]hept-2-yl-6-methyl-cyclohexanone, 4-bicyclo-[2.2.1]hept-2-yl-2-methyl-cyclohexanone, 4-bicyclo[2.2.1]-hept-2-yl-3-methyl-cyclohexanone, 2-[1,1'-bicyclopropyl]-2-yl-cyclohexanone, 2,6-bis[(4-methylphenyl)methyl]-cyclohexanone, 2,6-bis[(4-methylphenyl)methylene]-cyclohexanone, [4-[bis(4-methylphenyl)methylene]-2-ethyl-3-methyl]cyclohexanone, 2,6-bis(2-phenylethyl)-cyclohexanone, 2,6-bis(2-phenylmethyl)-cyclohexanone, 3-(2-cyclohexylethyl)-cyclohexanone, 4-(cyclohexyl-1-methylethyl)-cyclohexanone, 2,6-dicyclohexenyl-cyclohexanone, 4-(1,1-dimethylethyl)-phenyl-cyclohexanone, 3,3-dimethyl-5-[(4-methylphenyl)-methyl]-cyclohexanone, 2,6-dimethyl-2-(2-naphthalenyl)-cyclohexanone, 3,3-dimethyl-5-(1-naphthyl)-cyclohexanone, 2,6-dimethyl-2-phenyl-cyclohexanone, 3,3-dimethyl-2-phenyl-cyclohexanone, 4,4-dimethyl-2-phenyl-cyclohexanone, 2,2-dimethyl-6-phenyl-6-propyl-cyclohexanone, diphenyl-cyclohexanol having up to about 22 carbon atoms include cyclohexanone, 2,2- diphenyl-cyclohexanone, 2,3-diphenyl-cyclohexanone, 2,6-diphenyl-cyclohexanone, 3,3-diphenyl-cyclohexanone, 3,5-diphenyl-cyclohexanone, 4,4-diphenyl-cyclohexanone, 2-(1,2-diphenylethenyl)-cyclohexanone, 2-(diphenylmethyl)-cyclohexanone, 4,4-diphenyl-2-(2-propenyl)-cyclohexanone, 2-(3,3-diphenyl-2-propenyl)-cyclohexanone, 2-(3,3-diphenyl)-2-propenyl)-2-ethyl-cyclohexanone, 2-(3,3-diphenyl-2-propenyl)-2-methyl-cyclohexanone, 2-(3,3-diphenyl-2-propenyl)-2-propyl-cyclohexanone, 2-(1,3-diphenyl-propyl)-cyclohexanone, 2-ethyl-2-phenyl-cyclohexanone, 2-hexyl-cyclohexanone, 2-hexyl-3-methyl-cyclohexanone, methyldiphenyl-cyclohexanone, 2-methyl-4,4-diphenyl-cyclohexanone, 2-methyl-5,5-diphenyl-cyclohexanone, 6-methyl-2,2-diphenyl-cyclohexanone, 2-methyl-2-phenyl-cyclohexanone, 2-methyl-3-phenyl-cyclohexanone, 2-(3-methylphenyl)-cyclohexanone, 2-(4-methylphenyl)-cyclohexanone, 3-methyl-2-phenyl-cyclohexanone, 3-methyl-5-phenyl-cyclohexanone, 4-methyl-2-phenyl-cyclohexanone, 4-methyl-4-phenyl-cyclohexanone, 4-(2-methylphenyl)-cyclohexanone, 4-(3-methylphenyl)-cyclohexanone, 4-(4-methylphenyl)-cyclohexanone, 2-(1-methyl-1-phenylethyl)-cyclohexanone, 2-methyl-2-(phenylmethyl)-cyclohexanone, 2-methyl-6-(phenylmethyl)-cyclohexanone, 4-methyl-4-(phenyl-methyl)-cyclohexanone, 3-(4-methylphenyl)-2-phenyl-cyclohexanone, 2-(1-naphthyl)-cyclohexanone, 2-(2-naphthalenyl)-cyclohexanone, 2-phenyl-cyclohexanone, 3-phenyl-cyclohexanone, 4-phenyl-cyclohexanone, 2-(2-phenyl-ethyl)-cyclohexanone, 2-(phenylmethyl)-cyclohexanone, 2-(1-phenyl-propyl)-cyclohexanone, 2-(3-phenyl-propyl)-cyclohexanone, 3,3,5,5-tetramethyl-2-phenyl-cyclohexanone, 3,3,5-trimethyl-5-(2-methylphenyl)-cyclohexanone, 3,3,5-trimethyl-5(4-methylphenyl)-cyclohexanone, 3,3,5-trimethyl-5-(1-naphthyl)-cyclohexanone, 2,2,6-trimethyl-6-phenyl-cyclohexanone, 3,3,5-trimethyl-2-phenyl-cyclohexanone, 3,3,5-trimethyl-5-phenyl-cyclohexanone, 2,4,4-trimethyl-3-(2-phenylethyl)-cyclohexanone. Representative cyclohexanol derivatives useful as extractive solvents include 2,3-bis(4-methylphenyl)-cyclo-hexanol, 1,2-bis(phenyl-methyl)-cyclohexanol, 2,6-bis(phenyl-methyl)-cyclohexanol, 4-(1-cyclohexyl-1-methylethyl)-cyclohexanol, 1-[4-(1,1-dimethylethyl)phenyl]-cyclohexanol, 4-(1,1-dimethylethyl)-1-phenyl-cyclohexanol,5-(1,1-dimethyl-ethyl)-2-phenyl-cyclohexanol, 2,6-dimethyl-1-phenyl-cyclohexanol, 2,3-diphenyl-cyclohexanol, 4,4-diphenyl-cyclohexanol, 4-(diphenylmethyl)-cyclohexanol, 1-(1-methylethyl)-2-phenyl-cyclohexanol, 1-[4-(1-methylethyl)phenyl] cyclohexanol, 1-[[4-(1-methyl-ethyl)phenyl]methyl]-cyclohexanol, 5-methyl-2-(1-methyl-ethyl)-1-phenyl-cyclohexanol, 4-methyl-1-[2-(4-methylphenyl)ethyl]-cyclohexanol, 5-methyl-2-(1-methyl-1-phenylethyl)-cyclohexanol, 2-(2-methyl-1-naphthyl)cyclohexanol, 3-methyl-5-(1-naphthyl)-cyclohexanol, 5-methyl-2-(2-(2-naphthyl)propyl)-cyclohexanol, 6-methyl-2-(2-(2-naphthyl)propyl)-cyclohexanol, 1-(4-methylphenyl)-cyclohexanol, 2-methyl-1-phenyl-cyclohexanol, 2-(2-methylphenyl)-cyclohexanol, 3-methyl-1-phenyl-cyclohexanol, 3-(4-methylphenyl)-cyclohexanol, 4-methyl-1-phenyl-cyclohexanol, 4-methyl-4-phenyl-cyclohexanol, 4-(4-methylphenyl)-cyclohexanol, 2-methyl-1-(phenylmethyl)-cyclohexanol, 2-methyl-6-(phenylmethyl)-cyclohexanol, 4-methyl-1-(phenylmethyl)-cyclohexanol, 3-(4-methylphenyl)-2-phenyl-cyclohexanol, 2-(1-naphthyl)-cyclohexanol, 2-phenyl-cyclohexanol, 3-phenyl-cyclohexanol, 4-phenyl-cyclohexanol, 2-(2-phenylethyl)-cyclohexanol, 1-(phenylmethyl)-cyclohexanol, 2-(phenylmethyl)-cyclohexanol, 1,3,3,5-tetramethyl-5-(1-naphthyl)-cyclohexanol, 1,3,3,5-tetramethyl-5-(2-naphthyl)-cyclohexanol, 1,3,3,5-tetramethyl-5-phenyl-cyclohexanol, 3,3,5,5-tetramethyl-1-phenyl-cyclohexanol, 1,3,3-trimethyl-5-(1-naphthyl-cyclohexanol, 3,3,5-trimethyl-5-(1-naphthyl)-cyclohexanol, 3,3,5-trimethyl-1-phenyl-cyclohexanol, 2,4,4-trimethyl-3-(2-phenylethyl)-cyclohexanol.

The extractive solvents can be selected with boiling point and relative volatility optimal with respect to the constituents of the mixture to be separated. One or more members of the group consisting of hydrocarbyl-bicyclic derivatives of cyclohexanone or cyclohexanol having up to about 22 carbon atoms can be added to the mixture to obtain one or more members of the group consisting of cyclohexanone, cyclohexanol and their monomethyl derivatives as a product substantially free from members of the group consisting of phenol and/or cresol.

The extractive distillation procedure of the present invention can be performed in any manner feasible including but not limited to batch distillation or continuous distillation with one or more feeds and with or without product side streams taken out of the distillation column. A continuous operation is preferred. Batch operation is sometimes less desirable since it requires frequent recharging with fresh solvent and/or change in operation variables such as pressure, reflux rate or product quality during the distillation. In the extractive distillation of this invention, if conducted as continuous distillation, the extractive solvent can be added to the original feed mixture prior to feeding into the column, or added separately into the column. The quantity of the solvent added is so selected that due to the different characteristics of mixing the solvent with the compounds of the mixture, the composition activity coefficient combination, called activity, in the presence of the extractive solvent and one or more of the original compounds, say the first component, is significantly lower than that of the other original component or components, say the second component, in the presence of the extractive solvent so that a mixed liquid is formed in the bottom section of the column which is virtually free of the second component of the original mixture. If possible the third compound or solvent for an extractive distillation is so selected that this bottom mixture can be separated in downstream or subsequent operations such as fractional distillation.

Preferably an extractive distillation method is employed and the mixture is fed into a column and the extractive solvent is either mixed into the feed mixture or fed into the part of the column above the feeding point of the mixture. It is desired that in extractive distillation the third component or solvent is much higher boiling the mixture and thus easily separable by further distillation from the components of the original solution. In order to maintain the desired concentration profile in the extractive distillation column, the third component or solvent is introduced at a point in the column where its usefulness is maximum. The third component is sometimes, but not always, introduced at as liquid at the top section and is allowed to run down the column. By allowing sufficient trays above the solvent inlet to fractionate all of the solvent and the components not desired in the overhead product from overhead vapors, a substantially pure overhead product can be obtained. The solvent is removed from the bottom of the column with the other component. When employing a solvent which does not form azeotropes with either original component, the solvent is later separated from the extracted of the original mixture component by fractional distillation or other means as decantation, extraction or azeotropic distillation.

Depending on the nature of the components the specified pressure for the extractive distillation operation may or may not be critical. It may be desirable to perform the distillation under increased or under reduced pressure, e.g. 1/10th of an atmosphere, depending on the nature of the system and the economics involved. Among the advantages of reduced pressure operation are a further reduction of the losses through heat input required as low reboiler temperatures are employed, and reductions in the heat losses, and prevention of thermal decomposition of the organic materials.

In extractive distillation, ordinarily the temperature is higher at the bottom of the column than at the top. The gradient depends on the amount of material processed and refluxed. The temperature levels within the column are substantially dependent on the system pressure and the nature of the mixtures at any point within the column. If a pure compound is obtained as the overhead product, the temperature at the top of the column in either the gas or the liquid phase is close to the boiling point of the more volatile component under the pressure at that portion of the column.

The addition of extractive solvent to a mixture which is to be separated can be done either prior to distillation or as a separate distillation feed to any section of the column or the reboiler. In general, the bottoms stream containing the extractive solvent is separated in subsequent operations and the extractive solvent can be continuously returned into the extractive distillation column. Thus the need for fresh extractive solvent is limited only to makeup for losses. The extractive solvent preferably but not always flows countercurrently to the rising vapors.

Numerous types of equipment can be employed in the extractive distillation and solvent recovery process. Commonly used is a tray-type distillation column and the performance of other types of equipment is generally expressed in terms of equivalence to the tray column performance for comparison. The distillation column can also be a column packed with any packing material such as Raschig rings, pall or other high efficiency packing rings, Berl saddles or other saddle-like packing, sultzer or flexipack packing metal Intalox, mini rings or any packing or any grid or mesh type materials. As the selection of the nature or type of column internals, packing, trays or otherwise is immaterial to the distillation as long as sufficient equivalent of contact, in terms of transfer units, is provided and other requirements such as specified pressure drops, etc are met.

The number of plates or equivalent thereof employed in the present invention should be at least 5 and preferably 50 or its equivalent.

Extractive distillations according to the invention can be conducted with a 2.5 cm diameter Oldershaw column with varying number of trays and a varying number of feeds and varying operation conditions.

The separation and virtually total recovery of practically phenol free cyclohexanone and cyclohexanol from their mixtures with phenol can be obtained in the practice of this invention. In continuous extractive distillation, phenol and cyclohexanone and phenol and cyclohexanol are separated. When both cyclohexanone and cyclohexanol are present in the original mixture with phenol they are recovered together from their ternary phenol mixture as the only overhead product while the bottom stream consists of phenol and the extractive solvent with only traces of cyclohexanone and cyclohexanol. The concentration of said traces is controlled by varying the distillation column variables such as the number of trays, the overhead pressure, the number of feeds, the amount of solvent, the location of the feed trays and reflux ratio.

The alkanols, alkanones, cycloalkanols and/or cycloalkanones are recovered as either vapor products or liquids being the overhead condensate. The bottom stream consists of the extractive solvent and one or more members of the group consisting of phenol and cresol with insignificant traces of the overhead product which would be one or more members of the group consisting of alkanols, alkanones, cycloalkanols and/or cycloalkanones. The extractive solvent and the phenol and/or cresol can then be separated by other methods such as fractional distillation in a solvent recovery column.

The separation as disclosed permits substantially complete recovery of practically pure alkanols, alkanones, cycloalkanols and/or cycloalkanones.

The purity of the overhead condensate can be further increased by refluxing part of same. A certain amount of the overhead condensate is returned as reflux to the top section of the column.

Reflux ratio is defined as the amount of overhead condensate which is returned to the column compared to the amount withdrawn. Preferably, a reflux ratio from about 0.2 to 8:1 is employed in the present invention.

The amount of azeotrope breaking agent relative to feed depends on the pressure, the particular components, the number of trays, reflux ratio and other variables such as economics and efficient energy utilization. Preferably the molar amount of azeotrope breaking mixture relative to azeotrope forming feed is from about 0.5 to 5.

The process of the present invention is useful not only in the recovery alkanones, cycloalkanols and/or cycloalkanones but also in the recovery of phenol and/or cresol from their mixtures containing such compounds. In particular, the invention is useful for recovering cyclohexanone and cyclohexanol on one hand and phenol on the other hand from mixtures resulting from the catalytic hydrogenation of phenol cyclohexanol. The invention is also useful for separating products resulting from oxidative cleavage of cyclohexyl benzene.

EXAMPLE 1

A liquid mixture called herein "Feed-1" containing 30 mole % of cyclohexanone and 70 mole % phenol which by its nature is virtually the maximum boiling azeotropic mixture of these compounds was continuously fed into the 20th tray, counted from the reboiler, of a 2.5 cm diameter Oldershaw column assembly which consisted of a reboiler, 55 trays, a condenser and a reflux splitter. Another stream called herein "Feed 2" consisting of 84 mole % of 2-cyclohexyl-cyclohexanone and 16 mole % of 2-cyclohexyl-cyclohexanol was fed at the same time as the first feed above onto the 35th tray, counting from the bottom, of the same column.

The column was run for several hours at the absolute pressure of 75 mm Hg at the condenser and at a reflux ratio of 5:1 and samples were taken and analysed.

The data, given in Summary Table 1, show that cyclohexanone of high purity which contains 10 ppm or less phenol was recovered as the overhead product.

EXAMPLE 2

The apparatus of Example 1 was employed. Into a liquid mixture containing 14 mole % cyclohexanol and 86 mole % phenol which by its nature is virtually the maximum boiling azeotropic mixture of these compounds, an additional mixture of 89 mole % of 2-cyclohexyl-cyclohexanone and 11 mole % 2-cyclohexyl-cyclohexanol was added until the resulting mixture containing 5.14 mole % cyclohexanol, 31.63 mole % phenol, 53.07 mole % 2-cyclohexyl-cyclohexanone and 10.16 mole % 2-cyclohexyl-cyclohexanol was formed.

The four component mixture was fed continuously into the Oldershaw column. The column assembly consisted of a reboiler, fifty-five trays, an overhead condenser and a reflux splitter. The liquid mixture was continuously fed into Tray No. 25, counted from the bottom of said Oldershaw column. The column was run for several hours under the pressure of 120 mm Hg, measured at the condenser, and at a reflux ratio of 6:1 and samples were taken and analyzed.

The data, also presented in Summary Table 1, show that cyclohexanol of high purity which contains 5 ppm or less of phenol was recovered.

EXAMPLE 3

The apparatus of Example 1 was employed. To a liquid mixture containing 52.9 mole % cyclohexanol, 12.4 mole % cyclohexanone and 34.7 mole % phenol, an additional liquid mixture of 2-cyclohexyl-cyclohexanone and 2-cyclohexyl-cyclohexanol was added until the resulting mixture containing 27.7 mole % cyclohexanol, 6.5 mole % cyclohexanone, 18.2 mole % phenol, 27.6 mole % 2-cyclohexyl-cyclohexanone and 20 mole % 2-cyclohexyl-cyclohexanol was formed.

The five component mixture was fed continuously into an Oldershaw column. The column assembly consisted of a reboiler, fifty trays, an overhead condenser and a reflux splitter. The liquid mixture was continuously fed into Tray No. 20 counted from the bottom of said Oldershaw column. The column was run for several hours under a pressure of 200 mm Hg at the condenser and at a reflux ratio of 1:1 and samples were taken and analyzed. The data, given in the Summary Table, show the recovery of mixtures of cyclohexanone and cyclohexanol which contained less than 10 ppm phenol.

We claim:

1. A process for the separation by extractive distillation of one or more alkanols, alkanones, cycloalkanols and/or cycloalkanones from mixtures with phenol and/or cresol which comprises subjecting the mixture to extractive distillation conditions in the presence of an extractive solvent comprising one or more alkylated, unmodified cycloalkyl or aryl derivatives of cyclohexanone or cyclohexanol having up to about 22 carbon atoms.

2. The process as set forth in claim 1 wherein cycloalkanone having from about 5 to 9 carbon atoms is separated from a mixture with phenol and/or cresol.

3. The process as set forth in claim 2 wherein the ketone is cyclohexanone.

4. The process as set forth in claim 1 wherein cyclohexanol having from about 5 to 9 carbon atoms is separated from a mixture with phenol and/or cresol.

5. The process as set forth in claim 4 wherein the cycloalkanol is cyclohexanol.

6. The method as set forth in claim 1 wherein the phenol and/or cresol is phenol.

7. The method as set forth in claim 1 wherein the extractive solvent has a boiling point below 300° C.

8. The method as set forth in claim 1 wherein the extractive solvent comprises one or more members of the group consisting of bicyclic derivatives of cyclohexanone or cyclohexanol with phenyl, benzyl and/or cyclohexyl substituents, unmodified or further substituted with one or more alkyl-, cyclohexyl-, benzyl and/or phenyl groups adding less than nine carbon atoms to the bicyclic system.

9. The method as set forth in claim 1 wherein the extractive solvent comprises one or more members of the group consisting of phenyl and/or cyclohexyl derivatives of cyclohexanol and/or cyclohexanone.

10. The process as set forth in claim 9 wherein the extractive solvent is cyclohexyl cyclohexanone.

11. The method as set forth in claim 1 wherein the weight amount of extractive solvent employed relative to the mixture is from about 0.5 to 5.

12. The process as set forth in claim 1 wherein the mixture is introduced into a fractionation column and wherein the extractive solvent is introduced into said column at a different point thereof so that the extractive solvent flows countercurrently to the rising vapors of said mixture, said extractive solvent being present in an amount such that its concentration in the liquid at the point of its addition is at least 25 percent, withdrawing as overhead from the column alkanols, alkanones, cycloalkanols and/or cycloalkanones and removing from the bottom portion of the column a solution of phenol and/or cresol in the extractive solvent.

* * * * *

TABLE 1

| | CONCENTRATION MOLE % | | | | | | | | | |
|---|---|---|---|---|---|---|---|---|---|---|
| | EXAMPLE 2 | | | | EXAMPLE 3 | | | EXAMPLE 4 | | |
| Compound | Feed 1 | Feed 2 | Overhead | Bottoms | Feed | Overhead | Bottoms | Feed | Overhead | Bottoms |
| Cyclohexanone | 30 | — | >99.999 | 0.2 | — | — | | 6.5 | 15.2 | 1.6 |
| Cyclohexanone | — | — | — | — | 5.14 | >99.999 | 0.8 | 27.7 | 84.8 | 0.2 |
| Phenol | 70 | — | <5 ppm | 16.2 | 31.63 | <5 ppm | 33.31 | 18.2 | 5 ppm | 25 |
| 2-Cyclohexyl-cyclohexanone | — | 89 | 0 | 74.3 | 53.11 | | 59.28 | 27.6 | 0 | 40.5 |
| 2-Cyclohexyl-cyclohexanol | — | 11 | 0 | 9.2 | 10.12 | | 7.33 | 20.0 | 0 | 32.7 |
| Tray No. from bottom | 20 | 35 | 55 | 0 | 25 | 55 | 0 | 20 | 51 | 0 |
| Temperature °C. | | | | | | | | 145.8 | 127.8 | 180 |
| Pressure mm Hg | 747 | 747 | 75 | — | 747 | 118 | | 754 | 200 | |
| Rate cc/hr | 100 | 360 | 29 | 431 | 300 | 10 | 290 | 250 | 80 | 170 |
| Reflux Ratio | | | 5:1 | | | 6:1 | | | 1:1 | |